United States Patent [19]
Van Scharrenburg et al.

[11] Patent Number: 5,948,410
[45] Date of Patent: Sep. 7, 1999

[54] INFLUENZA VACCINE

[75] Inventors: Gustaar J. M. Van Scharrenburg; Rudi Brands, both of Weesp, Netherlands

[73] Assignee: Duphar International Research B.V., Weesp, Netherlands

[21] Appl. No.: 09/055,321

[22] Filed: Apr. 6, 1998

[30] Foreign Application Priority Data

Apr. 9, 1997 [EP] European Pat. Off. .............. 97201007

[51] Int. Cl.⁶ .......................... A61K 39/145; C12N 7/02; C12N 7/06
[52] U.S. Cl. .................................. 424/210.1; 424/209.1; 435/235.1; 435/236; 435/238; 435/239
[58] Field of Search .............................. 424/209.1, 210.1; 435/235.1, 236, 238, 239

[56] References Cited

U.S. PATENT DOCUMENTS

| | | |
|---|---|---|
| 4,317,811 | 3/1982 | Bertland et al. . |
| 4,500,513 | 2/1985 | Brown et al. . |
| 5,006,472 | 4/1991 | Dove et al. . |

FOREIGN PATENT DOCUMENTS

| | | | |
|---|---|---|---|
| 0370163 | 5/1990 | European Pat. Off. . | |
| 0389925 | 12/1995 | European Pat. Off. . | |
| 3237313 | 4/1984 | Germany .......................... | C12N 1/02 |
| 9010058 | 9/1990 | WIPO . | |
| 96/21035 | 4/1996 | WIPO ............................ | C12N 15/86 |
| 9615231 | 5/1996 | WIPO . | |
| 9704803 | 2/1997 | WIPO . | |

OTHER PUBLICATIONS

Palache et al, J. Infect. Dis. 176(Suppl. 1):S20–23, Aug. 1997.
Viral Vaccines and Residual Cellular DNA, Florian Horaud, Biologicals, vol. 23, pp. 225–228, 1995.
Bulletin of the World Health Organization, 1995, Cell Culture as a substrate for the production of influenza vaccines: Memorandum from a WHO meeting, pp. 431–435.
Medical Microbiology and Immunology, 1994, "Characterization and immunogenicity of a candidate subunit vaccine against varicella–zoster virus", pp. 105–117.
Vaccine, vol. 13, No. 16, pp. 1583–1588 (1995).
Journal of Virology, Aug. 1996, vol. 70, No. 8, p. 5519–5524.
Novel Strategies in Design and Production of Vaccines, 1996, pp. 141–151, Ed. Cohen et al, Plenum Press, N.Y.
Brands et al, Proceedings of the Third International Conference on Options for the Control of Influenza, Cairns, Australia, May 4–9, 1996, "Options for the Control of Influenza III", pp. 683–693, Ed, Brown et al, Elsevier Amsterdam.
Huyge, B. et al. Human Gene Therapy 6: 1403–1416, Nov. 1995.
Merck–USA. Chim. Oggi 10 (4): 49–51, Apr. 1992.
Loewer, J. Cytotechnology 14, supl. 1, 5.1 (abstract only), 1994.
Hofschneider, P.H. Journal of Medical Virology 31: 65–66, 1990.

*Primary Examiner*—Mary E. Mosher
*Attorney, Agent, or Firm*—Stevens, Davis, Miller & Mosher, L.L.P.

[57] ABSTRACT

The present invention is concerned with an Influenza surface antigen vaccine obtainable by production from Influenza Viruses propagated on animal cell culture and having a host cell DNA content equal to or less than 25 pg per dose. The present invention is also concerned with a method for the preparation of surface antigen proteins from Influenza Viruses propagated on an animal cell culture comprising the subsequent steps of:

a. treatment of the whole virus containing fluid obtained from the cell culture with a DNA digesting enzyme, and b. adding a cationic detergent, followed by isolation of the surface antigen proteins.

9 Claims, No Drawings

INFLUENZA VACCINE

The present invention is concerned with Influenza surface antigen vaccines obtainable by production from Influenza Viruses propagated on animal cell culture and with a method for the preparation of surface antigen proteins of Influenza Viruses propagated on an animal cell culture.

The body of the Influenza Virus has a size of about 125 nm and it consists of a core of ribonucleic acid (RNA) associated with the nucleoprotein, surrounded by a viral envelope with a lipid bilayer structure. The inner layer of the viral envelope is composed predominantly of matrix proteins and the outer layer contains most of the host-derived lipid material.

The so-called "surface proteins", neuraminidase (NA) and hemagglutinine (HA), appear as spikes on the surface of the viral body.

Most of the commercially available inactivated influenza vaccines are so-called "split vaccines" or "subunit vaccines".

"Split vaccines" are prepared by the treatment of the whole Influenza Virus with solubilizing concentrations of detergents and subsequent removal of the detergent and of the bulk of the viral lipid material.

"Subunit vaccines" against influenza unlike "split vaccines" do not contain all viral proteins. Instead, "subunit vaccines" are enriched in surface proteins responsible for eliciting the desired virus neutralising (hence protecting) antibodies upon vaccination.

Most of the commercially available Influenza vaccines are derived from Influenza Viruses cultured on embryonated chicken eggs. It is widely recognised, however, that the egg-derived production of Influenza virus for vaccine purposes has several disadvantages:

1. Such production process is rather vulnerable due to the varying (micro)biological quality of the eggs.

2. The process completely lacks flexibility if suddenly demand increases, i.e. in case of a serious epidemic or pandemic, because of the logistic problems due to non-availability of large quantities of suitable eggs.

3. Vaccines thus produced are contra-indicated for persons with a known hypersensitivity to chicken and/or egg proteins.

A solution for these problems may reside in tissue culture derived production of Influenza Virus. It is considered that such production method has many advantages:

1. Tissue culture cell lines are available in well defined cell bank systems free of (micro)biological contaminants, whereby the batch-to-batch consistency is greatly improved and a product of higher quality is obtained.

2. It will increase the chances to have sufficient vaccine available in case of a serious epidemic or pandemic threat.

3. The resulting Influenza Virus material will be better suited for alternative routes of administration (oral, nasal, inhaled).

4. From the WHO's point of view, the technology will allow to postpone the yearly vaccine composition recommendation (from mid-February to mid-March), increasing the matching of the vaccine with the circulating strains.

Nevertheless, an important problem remains in relation to tissue culture of Influenza virus too, as genetic material from continuous cell lines may remain present in the vaccine.

Such problem poses a risk which, if not remedied, may lead regulatory authorities to decline requests for market allowance for such Influenza vaccines for safety reasons. E.g. the U.S. Food and Drug Administration demands that biotechnological products for human use do not contain more than 100 pg of host cell DNA per dose.

Therefore, the present invention provides a method for the preparation of Influenza Virus surface antigen for vaccine purposes which is safe and does not contain non-acceptable amounts of deleterious genetic material, and meets the requirements set by the regulatory authorities. However, it was considered desirable and surprisingly also attainable to prepare influenza vaccines with a host cell DNA content considerably lower than 100 pg/dose.

Accordingly, the present invention is concerned with an Influenza surface antigen vaccine obtainable by production from Influenza Viruses propagated on animal cell culture and having a host cell DNA content equal to or less than 25 pg per dose.

In a specific embodiment the instant invention provides a method for the preparation of surface antigen proteins useful for preparing such low DNA influenza vaccine from Influenza Viruses propagated on an animal cell culture comprising the subsequent steps of:

a. treatment of whole virus containing fluid obtained from the cell culture with a DNA digesting enzyme, and b. adding a cationic detergent, followed by isolation of the surface antigen proteins.

The method according to the present invention may be applied during the production of vaccines containing diverse Influenza Viruses strains such as the viruses typical for Human Influenza, Swine Influenza, Equine Influenza and Avian Influenza.

The animal cell culture according to the present invention may contain either primary cell, such as Chicken Embryo Fibroblasts (CEF) or a continuous cell line, such as Madin Darby Canine Kidney Cells (MDCK), Chinese Hamster Ovary Cells (CHO) and Vero cells.

The treatment of the whole virus containing fluid with DNA digesting enzyme may be carried out directly in the fermenter, optionally already during the cell culturing and viral propagation process.

Suitable examples of DNA digesting enzymes are DNase (e.g. classified under EC 3.1.21 and EC 3.1.22) and nucleases (e.g. classified under EC 3.1.30 and 3.1.31).

Suitable cationic detergents according to the present invention predominantly consist of a compound of the general formula

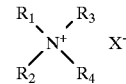

wherein $R_1$, $R_2$ and $R_3$ are the same or different and each signifies alkyl or aryl, or $R_1$ and $R_2$, together with the nitrogen atom to which these are attached form a 5- or 6-membered saturated heterocyclic ring, and $R_3$ signifies alkyl or aryl, or $R_1$, $R_2$ and $R_3$ together with the nitrogen atom to which these are attached, signify a 5- or 6-membered heterocyclic ring, unsaturated at the nitrogen atom, $R_4$ signifies alkyl or aryl, and X signifies an anion.

Examples of such cationic detergents are cetyltrimethylammoniumsalts, such as cetyltrimethylammonium bromide (C.T.A.B.), and myristyltrimethylammonium salt. Suitable detergents are also lipofectine, lipofectamine, DOTMA.

Optionally these cationic detergents can be supplemented with a non-ionic detergent, such as Tween.

The isolation of the surface antigen proteins subsequent to the detergent treatment step e.g. may comprise the steps of:

1. Separation of the RNP particle (body) from the surface antigen proteins, e.g. by centrifugation or ultrafiltration, and
2. Removal of the detergent from the surface antigen proteins, e.g. by hydrophobic interaction of the detergent wit a suitable resin (such as Amberlite XAD-4) and/or by ultra(dia)filtration.

Surprisingly, the process according to the present invention yields a product which is extremely low in its content of animal cell-derived DNA. DNA concentrations as low as 25 pg/dose and in many instances even as low as 10 pg/dose are easily attainable.

The surface antigen proteins may be processed to prepare the Influenza vaccine, e.g. by adding buffer (e.g. PBS) and/or mixing with antigens from other influenza virus serotypes Optionally concentration of the surface antigen is required for further vaccine preparation.

EXAMPLE 1

A. Virus Multiplication

1. Influenza virus of the antigen type B/Yamagata is multiplied on Madin Darby Canine Kidney (MDCK) cells (ATCC CCL34) in a fermenter by incubating the seed virus with the cells for two days at 35° C.
2. Next, the pH of the fermenter fluid is raised to 8.0 by the addition of dilute sodium hydroxide and Benzon nuclease is added to a final concentration of 1000 units (1 $\mu$g) per liter.
3. Incubation is proceeded at 35° C. for another four hours.

B. Virus Isolation

1. The fluid is filtered through a depth filter with a nominal pore size of 0.5 micron to remove the cellular debris.
2. Subsequently, the influenza virus is concentrated and purified by ultrafiltration using a membrane with a molecular weight cut-off of 300.000.
3. Sucrose is added to the concentrate to a final concentration of 30% (w/v) after which formaldehyde is added to a final concentration of 0.015% (w/v). This mixture is stirred at 2–8° C. for 72 hours.
4. Next the virus concentrate is diluted five-fold with phosphate buffered saline and loaded onto a affinity column containing Amicon Cellufine Sulphate. After removing impurities by washing with phosphate buffered saline the virus is eluted with a solution of 1.5 molar sodium chloride in phosphate buffered saline. The eluate is concentrated and desalted by ultrafiltration using a membrane with a molecular weight cut-off of 300.000.

C. Subunit Isolation

1. The non-ionic detergent Tween-80 is added to a final concentration of 300 $\mu$g/ml and cetyltrimethylammonium bromide is added to a final concentration of 750 $\mu$g/ml. This mixture is stirred at 4° C. for three hours after which the RNP particle is separated from the surface antigen proteins by centrifugation.
2. The supernatant is stirred with Amberlite XAD-4 overnight at 2–8° C. to remove the detergents. The Amberlite is removed by filtration and the filtrate is subsequently subjected to sterile filtration by passage through a 0.22 μm filter.

Throughout the above process the host cell DNA content of samples was analysed according to a validated test, based on slot blot hybridisation using a 32 P-labelled canine DNA probe.

The results of the DNA assay performed after various steps are given in the following Table (In this Table the DNA amount per IVV dose is expressed in picogram per 50 μg HA).

TABLE

| Sample | DNA content | After step |
|---|---|---|
| Fermenter fluid 48 hpi | 19.000.000 | A1 |
| Fermenter fluid after nuclease treatment | 370.000 | A2 |
| Fluid after pre-filtration | 10.000 | B1 |
| Concentrate after ultrafiltration | 4350 | B2 |
| Fluid after inactivation and affinity chromatography | 4200 | B4 |
| Supernatant after Tween/C.T.A.B. treatment and centrifugation | <25 | C1 |
| Filtrate after detergent removal | <25 | C2 |

EXAMPLE 2

Multiplication, purification, inactivation and cleavage of the virus are affected as in Example 1.

Benzon nuclease treatment of the fermenter fluid during the last hours of the virus multiplication (Steps A2 and A3), using the pH of the multiplication medium (Step A1), yields similar results with respect to DNA removal. DNase I, although required in higher concentrations, is equally effective in removing host cell DNA (during Steps A1–A3). Similar results can be obtained using other endonucleases.

EXAMPLE 3

The process is effected as in Example 1 or 2, except that removal of the cell debris (Step B1) is effected by centrifugation.

EXAMPLE 4

The process is effected as in Example 1, 2 or 3, except that the virus is concentrated and purified (Step B2) from the fermenter fluid by centrifuging in a continuous flow zonal centrifuge e.g. Electro-Nucleonics (model RK) using a sucrose gradient in e.g. phosphate buffered saline.

EXAMPLE 5

The process is effected as in Example 1 to 4, except that the addition of cetyltrimethylammonium bromide solution in Step C1 is replaced by addition of a solution of cetylpyridinium bromide, myristyl-trimethylammonium bromide, benzetonium chloride, methylbenzethonium chloride, decamethonium chloride or stearyldimethylbenzylammonium bromide. Similar results with respect to the removal of host cell DNA are obtained.

EXAMPLE 6

The process is effected as described in example 1, except that addition of sucrose is performed after affinity column chromatography and formaldehyde is added to 0.05% (w/v) maximum for 120 hours.

EXAMPLE 7

The methods according to Examples 1, 2, 3, 4 and 6 were applied successfully for preparing low DNA vaccines from Influenza Viruses of the strains B/Harbin, B/Panama, A/Texas (H1N1), A/Taiwan (H1N1), A/Johannesburg (H3N2) and A/Wuhan (H3N2) as well.

We claim:

1. Influenza surface antigen vaccine obtainable by production from Influenza Viruses propagated on animal cell culture and having a host cell DNA content equal to or less than 25 pg per dose.

2. Influenza surface antigen vaccine according to claim 1, having a host cell DNA content less than 10 pg per dose.

3. Method for the preparation of surface antigen proteins from Influenza Viruses propagated on an animal cell culture comprising the subsequent steps of:

a. treatment of the whole virus containing fluid obtained from the cell culture with a DNA digesting enzyme, and
   b. adding a cationic detergent, followed by isolation of the surface antigen proteins.

4. Method according to claim 3, wherein the treatment with DNA digesting enzyme takes place during propagation of the Influenza Viruses in the cell culture.

5. Method according to claim 3 wherein the cationic detergent predominantly consists of a compound of the general formula

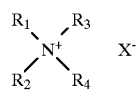

wherein $R_1$, $R_2$ and $R_3$ are the same or different and each signifies alkyl or aryl, or $R_1$ and $R_2$, together with the nitrogen atom to which these are attached form a 5- or 6-membered saturated heterocyclic ring, and $R_3$ signifies alkyl or aryl, or $R_1$, $R_2$ and $R_3$ together with the nitrogen atom to which these are attached, signify a 5- or 6-membered heterocyclic ring, unsaturated at the nitrogen atom, $R_4$ signifies alkyl or aryl, and X signifies an anion.

6. Method according to claim 3 wherein the cationic detergent predominantly comprises cetyltrimethylammoniumbromide.

7. Method according to claim 3 wherein the cationic detergent is supplemented with a non-ionic detergent.

8. Method according to claim 3 wherein the Influenza Viruses are propagated on an animal cell line.

9. Method according to claim 3 wherein the Influenza Viruses are propagated on MDCK cells.

* * * * *